(12) United States Patent
Nakata et al.

(10) Patent No.: US 9,915,601 B2
(45) Date of Patent: Mar. 13, 2018

(54) METHOD FOR EXAMINING MICROORGANISMS AND EXAMINATION APPARATUS FOR MICROORGANISMS

(71) Applicant: SATAKE CORPORATION, Tokyo (JP)

(72) Inventors: Akiko Nakata, Hiroshima (JP); Shinya Fushida, Hiroshima (JP); Akira Eto, Hiroshima (JP); Masanori Matsuda, Hiroshima (JP); Yukio Hosaka, Hiroshima (JP)

(73) Assignee: SATAKE CORPORATION, Tokyo (JP)

( * ) Notice: Subject to any disclaimer, the term of this patent is extended or adjusted under 35 U.S.C. 154(b) by 0 days.

(21) Appl. No.: 14/423,134

(22) PCT Filed: Aug. 23, 2013

(86) PCT No.: PCT/JP2013/072521
§ 371 (c)(1),
(2) Date: Feb. 23, 2015

(87) PCT Pub. No.: WO2014/030729
PCT Pub. Date: Feb. 27, 2014

(65) Prior Publication Data
US 2015/0219548 A1    Aug. 6, 2015

(30) Foreign Application Priority Data

Aug. 24, 2012 (JP) ................................. 2012-185523
Sep. 11, 2012 (JP) ................................. 2012-199556

(51) Int. Cl.
*G01N 1/00* (2006.01)
*G01N 15/00* (2006.01)
(Continued)

(52) U.S. Cl.
CPC ......... *G01N 15/1456* (2013.01); *C12M 41/36* (2013.01); *C12Q 1/06* (2013.01);
(Continued)

(58) Field of Classification Search
CPC ... C12M 41/36; C12Q 1/06; G01N 2015/035; G01N 2201/12; G01N 2201/068; G01N 21/645; G01N 15/1456
See application file for complete search history.

(56) References Cited

U.S. PATENT DOCUMENTS 5,389,544 A    2/1995    Sugata et al.
6,375,139 B1   4/2002    Murray et al.
(Continued)

FOREIGN PATENT DOCUMENTS

CN    1826521 A    8/2006
CN    201497706 U  6/2010
(Continued)

OTHER PUBLICATIONS

Chinese Office Action for Application No. CN2013800438293 dated Dec. 30, 2015.
(Continued)

*Primary Examiner* — Nathan A Bowers
(74) *Attorney, Agent, or Firm* — Orion Consulting, Ltd.; Joseph P. Farrar

(57) ABSTRACT

An examination apparatus 1 for microorganisms for measuring an amount of microorganisms in a sample solution, the apparatus including stirring and mixing means 7 for stirring and mixing the sample solution into which a sample and a fluorescent staining reagent are added, in a sample container 5 formed of a material allowing light to pass through, an excitation light source 10 including a light source that irradiates an irradiation target surface of the sample container 5 with excitation light while the sample
(Continued)

solution is being stirred by the stirring and mixing means 7, light receiving means 14 for detecting light and converting the light resulting from a fluorescent emission caused by excitation light from the excitation light source 10, into an electric signal, and control means 23 for detecting the number of emissions based on the electric signal from the light receiving means 14 and calculating the amount of the microorganisms contained in the sample in the sample container 5 based on the number of emissions.

8 Claims, 21 Drawing Sheets

(51) Int. Cl.
  *G01N 21/00* (2006.01)
  *G01N 15/14* (2006.01)
  *C12M 1/34* (2006.01)
  *C12Q 1/06* (2006.01)
  *G01N 21/64* (2006.01)

(52) U.S. Cl.
  CPC ... *G01N 21/645* (2013.01); *G01N 2015/0065* (2013.01); *G01N 2015/035* (2013.01); *G01N 2015/1486* (2013.01); *G01N 2021/6471* (2013.01); *G01N 2021/6478* (2013.01); *G01N 2201/062* (2013.01); *G01N 2201/068* (2013.01); *G01N 2201/06113* (2013.01); *G01N 2201/12* (2013.01)

(56) References Cited

U.S. PATENT DOCUMENTS

| | | |
|---|---|---|
| 2002/0119438 A1 | 8/2002 | Kato |
| 2005/0064582 A1 | 3/2005 | Wittwer et al. |
| 2006/0177869 A1 | 8/2006 | Heal et al. |
| 2007/0298451 A1 | 12/2007 | Ribault et al. |
| 2008/0272283 A1* | 11/2008 | Feldsine ............... G01N 21/76 250/229 |
| 2008/0279441 A1 | 11/2008 | Matsuo |
| 2009/0093045 A1* | 4/2009 | Takenaka ............. G01N 15/147 435/287.1 |
| 2011/0042582 A1* | 2/2011 | Ingber ................. G01N 21/0303 250/458.1 |
| 2012/0071342 A1* | 3/2012 | Lochhead .......... G01N 21/6452 506/9 |
| 2012/0221256 A1 | 8/2012 | Heal et al. |
| 2013/0011848 A1* | 1/2013 | Boege ....................... B01L 7/52 435/6.12 |
| 2013/0130369 A1* | 5/2013 | Wilson ................. B01L 3/5085 435/289.1 |
| 2014/0127794 A1 | 5/2014 | Kawashima |
| 2015/0329894 A1 | 11/2015 | Roscoe et al. |
| 2015/0337350 A1* | 11/2015 | Ram ....................... C12Q 1/04 435/39 |

FOREIGN PATENT DOCUMENTS

| | | |
|---|---|---|
| CN | 101906384 A | 12/2010 |
| DE | 3127560 A1 | 2/1983 |
| EP | 0881489 A1 | 12/1998 |
| JP | 3-43069 A | 2/1991 |
| JP | 3-272697 A | 12/1991 |
| JP | H04281441 A | 10/1992 |
| JP | 8-173197 A | 7/1996 |
| JP | 10-99096 A | 4/1998 |
| JP | 2002340901 A | 11/2002 |
| JP | 2004061438 A | 2/2004 |
| JP | 2004305173 A | 11/2004 |
| JP | 2006-42655 A | 2/2006 |
| JP | 2006227117 A | 8/2006 |
| JP | 2006300632 A | 11/2006 |
| JP | 2006-340686 A | 12/2006 |
| JP | 2007-71743 A | 3/2007 |
| JP | 2007-135582 A | 6/2007 |
| JP | 20085840 A | 1/2008 |
| JP | 200829271 A | 2/2008 |
| JP | 2009-85898 A | 4/2009 |
| JP | 2009201421 A | 9/2009 |
| JP | 2009-219455 A | 10/2009 |
| JP | 2010112809 A | 5/2010 |
| JP | 2010181205 A | 8/2010 |
| JP | 2010249575 A | 11/2010 |
| JP | 2011013167 A | 1/2011 |
| JP | 201136188 A | 2/2011 |
| JP | 2011507524 A | 3/2011 |
| JP | 2011153945 A | 8/2011 |
| JP | 2012-53056 A | 3/2012 |
| WO | 2001010881 A1 | 2/2001 |
| WO | 20020034091 A1 | 5/2002 |
| WO | 2005098022 A1 | 10/2005 |
| WO | 2006084283 A2 | 8/2006 |
| WO | 2007118209 A2 | 10/2007 |
| WO | 2011088014 A2 | 7/2011 |
| WO | 2011128893 A2 | 10/2011 |

OTHER PUBLICATIONS

Ito, Akihide et al., "Development of Flow Cytometry System to Count Bacteria in the Ballast Water", Mitsui Shipbuilkdign Technical Report No. 195 (Oct. 2008).
International Search Report for PCT/JP2013/072521 dated Sep. 24, 2013.
Alimova et al., "Bacteria-clay interactions investigated by light scattering and phase contrast microscopy", Proc. of SPIE, vol. 6094, p. 1-8 (2006).
Pham et al., "Bactericidal Activity of Glycinecin A, a Bacteriocin Derived from Xanthomonas campestris pv. glycines, on Phytopathogenic Xanthomonas campestris pv. vesicatoria Cells", Applied And Environmental Microbiology, vol. 70:8, p. 1-10 (2004).
Extended European Search Report for European Application No. 13830429.0 dated Feb. 29, 2016.
International Preliminary Report for PCT/JP2013/072521 dated Feb. 24, 2015.
Written Opinion for PCT/JP2013/072521 dated Sep. 24, 2013.
"Microbiology", Chief editor: Lu Fuping, p. 329, China Light Industry Press, Jul. 2005 [Submitted with Machine Translation].
"Food Safety Test, Detection Technology and Method", Chief editor: Chen Fusheng, p. 258, Chemical Industry Press, Sep. 2010 [Submitted With Machine Translation].
Applied and Environmental Microbiology, 2004, vol. 70, No. 8, pp. 4,486-4,490.
Bun Heisei, Elec Exchange 2, Aug. 24, 2005, B5 edition (Google translation submitted).
Seiichiro Hara, Mathematical Processing of Postgraduate Lecture Measurement Information, Nov. 7, 2003 (Google translation submitted).
Noise Measurement Using EMI Filter, Guidance for Application, I, Murata Manufacturing Co., Ltd., Oct. 11, 2016.
Japanese Office Action dated Sep. 5, 2017.
Australian Office Action for Application No. 2013306701 dated Dec. 14, 2017.

\* cited by examiner

NO SLIT

SLIT PROVIDED

METHOD FOR EXAMINING MICROORGANISMS AND EXAMINATION APPARATUS FOR MICROORGANISMS

TECHNICAL FIELD

The present invention relates to a method for examining microorganisms and an examination apparatus for microorganisms, and in particular, to a method for examining microorganisms such as planktons which are contained and live in ballast water or the like, the method being suitable for detecting the microorganisms, and an examination apparatus for microorganisms.

BACKGROUND ART

A ship that is not carrying cargo sails while being loaded with ballast water in order to stabilize the ship, and discharges the ballast water in a marine area in which cargo is loaded on the ship.

The ballast water is normally discharged in a marine area different from the marine area where the cargo is loaded on the ship. Thus, microorganisms such as planktons and bacteria contained in the ballast water may be carried to a marine area different from the native habitat of the microorganisms, disadvantageously posing problems such as disruption of ecosystem.

To deal with such problems, international rules for the regulation of ballast water have been formulated, and the International Convention for the Control and Management of Ship's Ballast Water and Sediments (Ballast Water Management Convention) has been adopted.

In the "Guidelines for Ballast Water Sampling (G2)", "Ballast Water Discharge Standards (D-2)" related to the Ballast Water Management Convention, the allowable population of microorganisms contained and living in the ballast water discharged from the ship is specified for each type of microorganisms based on the minimum size. For example, the allowable population is specified as at most $10/m^3$ for microorganisms with a minimum size of at least 50 μm (hereinafter referred to as "L size organisms") and as at most 10/mL for microorganisms with a minimum size of at least 10 μm and less than 50 μm (hereinafter referred to as "S size organisms").

As a method for measuring microorganism cells living in water such as ballast water, a method described in Patent Literature 1 has been known.

In the method described in Patent Literature 1, first, a chemical substance reacting with an enzyme or a coenzyme present in living cells of microorganisms to generate a fluorescent substance in the cells is allowed to act on a measurement target sample containing the microorganisms. The chemical substance and the microorganisms are then mixed and contacted with one another for given time, and the sample is irradiated with light with a wavelength needed to excite the fluorescent substance generated in the cells. Furthermore, in this method for measuring the living cells of the microorganism cells, light emitted by the individual microorganisms in the sample is measured as the number of points.

This method significantly reduces measurement time that needs to be 10 hours to several tens of hours in a conventional agar culture method, to at most 10 minutes. Furthermore, since means for optically and electrically detecting and measuring light emitted by viable bacteria as points has been established, the number of viable bacteria can be directly, automatically counted. Thus, advantageously, a sterilization apparatus can be promptly controlled, and product quality can be expeditiously managed.

However, in the method described in Patent Literature 1, measured values may vary depending on the type of water, temperature, the type of a stain, concentration, staining time, and the like.

As other methods, for example, the following are known: an examination apparatus for microorganisms that passes sea water pumped up using a water pump through flow cells and performs image measurement in order to determine whether or not the discharge standards are met when the ballast water is discharged (for example, Patent Literature 2), and an examination apparatus for microorganisms which passes sea water pumped up using a water pump through filter units with different apertures and which allows microorganisms on the filters to emit light to count the number of the microorganisms (for example, Patent Literature 3).

The examination apparatus for microorganisms described in Patent Literature 2 includes a staining section that allows a liquid specimen to flow while staining organisms with living cells present in the specimen, a concentration section that allows the stained specimen to flow while concentrating the specimen so as to increase the concentration of the organisms, an individual measurement section that acquires image information on individuals including the organisms in the concentrated specimen, and control means for measuring the organisms based on the image information on the individuals output by the individual measurement section.

This allows sequential execution of a staining step of staining the organisms in the liquid of the specimen, a step of concentrating the organisms in the liquid, a step of acquiring information on the organisms in the liquid, and the like. Thus, compared to a technique for individually executing schemes, this technique has the following advantages. Waiting time until a part of a specimen on which one step has been executed proceeds to the next step can be drastically reduced or eliminated. Furthermore, information indicating whether the organisms are alive or dead can be acquired, the information being stable in a sense that the condition of staining during the waiting time is prevented from being degraded.

However, the examination apparatus for microorganisms described in Patent Literature 2 sequentially passes sea water pumped up using the water pump through various steps, leading to the need for a large-scale apparatus and increased manufacturing costs. At least several hours may be needed to complete the measurement.

Furthermore, the examination apparatus for microorganisms described in Patent Literature 3 is characterized by including a step of passing sea water though filter units with three types of filters arranged in series and having different apertures, a step of causing the microorganisms collected and living in the filters to perform one of color production, light emission, and fluorescence production, and a step of detecting one of the color production, light emission, and fluorescence production and counting the number of the microorganisms in the ballast water or sea water by means of image analysis.

Thus, the microorganisms can be captured according to the stepwise size thereof, consequently enabling expeditious determination of whether allowable residue standards regulated according to the size of microorganisms are met.

However, as is the case with Patent Literature 1, the examination apparatus for microorganisms described in Patent Literature 3 passes sea water pumped up using the water pump through various steps, possibly leading to the need for a large-scale apparatus and increased manufacturing costs.

CITATION LIST

Patent Literature

[Patent Literature 1] Japanese Patent Laid-Open No. 3-43069
[Patent Literature 2] Japanese Patent Laid-Open No. 2009-85898
[Patent Literature 3] Japanese Patent Laid-Open No. 2007-135582

SUMMARY OF INVENTION

Technical Problem

With the above-described problems in view, it is a technical object of the present invention to provide a method for examining microorganisms in ballast water and an examination apparatus for microorganisms which allow the amount of the microorganisms to be easily and quickly measured with high accuracy.

Solution to Problem

To accomplish the object, the present invention has taken technical measures by providing an examination apparatus for microorganisms for measuring an amount of microorganisms in a sample solution, the apparatus including: stirring and mixing means having a sample container formed of a material allowing light to pass through, for stirring and mixing the sample solution in the sample container, an excitation light source that irradiates the sample container with excitation light; light receiving means for detecting light and converting the light into an electric signal; and control means for calculating the amount of the microorganisms contained in a sample in the sample container, in which the sample solution is prepared by adding a fluorescent staining reagent that stains the microorganisms to the sample, the light receiving means detects a fluorescent emission from the sample solution resulting from irradiation with the excitation light from the excitation light source, and the control means detects the number of emissions based on an electric signal from the light receiving means to calculate the amount of the microorganisms contained in the sample in the sample container.

Thus, the sample and the fluorescent staining reagent that stains the microorganisms are added into the sample container, and the stirring and mixing means stirs and mixes the sample solution. Next, with the sample solution being stirred, excitation light is allowed to enter the sample container, and moreover, the light receiving means receives fluorescent emissions from the microorganisms. Consequently, compared to an examination apparatus for microorganisms that measures the sample solution kept stationary without stirring, the examination apparatus for microorganisms according to the present invention allows the microorganisms to emit bright light in a very short time, enabling the amount of microorganisms in ballast water to be easily and quickly measured. Furthermore, the apparatus according to the present invention is not of a flow type and can thus be downscaled, allowing manufacturing costs to be reduced.

Additionally, an embodiment of the invention is characterized by including filtering means between the light receiving means and the control means, in which the filtering means filters out noise of a low frequency component and noise of a high frequency component contained in the electric signal from the light receiving means.

Thus, before the electric signal is loaded into the control means, the filtering means filters out disturbance, allowing the electric signal commensurate with the amount of fluorescent emissions from the microorganisms to be definitely distinguished from the disturbance. This prevents a possible error in the measurement of the amount of the microorganisms and a disadvantageous variation in measured values, enabling stable measurement.

An embodiment of the invention is characterized in that the filtering means is a band pass filter with a high pass filter and a low pass filter coupled together.

An embodiment of the invention is characterized in that the excitation light source is disposed so as to irradiate the sample container with the excitation light in such a manner that the excitation light is orthogonal to the sample container, and the light receiving means is disposed so as to receive the fluorescent emission at an angle orthogonal to the excitation light from the excitation light source.

Thus, the excitation light from the excitation light source is prevented from directly entering the light receiving means, and the thickness portion of the fluorescent emission is made thinner (for example, the width of an emission portion, which is conventionally 20 mm to 30 mm, is reduced to a width M (3 mm) as depicted in FIG. 2, and thus, the thickness portion is thinner). This significantly clarifies the difference in the amount of light between a background and the fluorescent emissions from the microorganisms, improving detection accuracy for the fluorescent emissions from the microorganisms.

Furthermore, an embodiment of the invention is characterized in that a slit member is provided between the light receiving means and the sample container.

Thus, the area of a fluorescent emission from the background, which contributes to noise, is reduced. This increases the signal ratio of the fluorescent emissions from the microorganisms to the fluorescent emission from the background, and improves the detection accuracy for the fluorescent emissions from the microorganisms.

Moreover, an embodiment of the invention is characterized in that parallel-light converting means for converting light from the excitation light source into parallel light is provided between the excitation light source and the sample container.

Thus, the excitation light from the excitation light source is restrained from being spread so that an irradiation target surface of the sample container is irradiated with parallel light. Consequently, the thickness portion of the fluorescent emission from the background is made thinner. This increases the signal ratio of the fluorescent emissions from the microorganisms to the fluorescent emission from the background, improving the detection accuracy for the fluorescent emissions from the microorganisms.

An embodiment of the invention is characterized in that the parallel-light converting means is formed by drilling a threaded hole in a flat plate.

Thus, an inexpensive material can be used to allow the angle of the excitation light from the excitation light source to be forcibly set by the threaded hole, enabling a reduction in the directivity angle of light radiated through the threaded hole. Consequently, the thickness portion of the fluorescent emission from the background is made thinner. This increases the signal ratio of the fluorescent emissions from the microorganisms to the fluorescent emission from the background, improving the detection accuracy for the fluorescent emissions from the microorganisms.

Furthermore, an embodiment of the invention is characterized in that the parallel-light converting means is formed of a convex lens.

Thus, an inexpensive material can be used to reduce the directivity angle of the excitation light from the excitation light source. Consequently, the thickness portion of the fluorescent emission from the background is made thinner. This increases the signal ratio of the fluorescent emissions from the microorganisms to the fluorescent emission from the background, improving the detection accuracy for the fluorescent emissions from the microorganisms.

An embodiment of the invention is a method for examining microorganisms in a sample solution to measure an amount of the microorganisms in a sample solution, the method including: a stirring and mixing step of stirring and mixing, in the sample container, the sample solution in which a fluorescent staining reagent that stains the microorganisms is added to a sample; an excitation step of irradiating the sample container with excitation light; a light receiving step of detecting a fluorescent emission from the sample container resulting from the irradiation with the excitation light, and converting the fluorescent emission into an electric signal; and a microorganism number estimating step of detecting the number of emissions based on the electric signal resulting from the conversion in the light receiving step, and calculating the amount of the microorganisms contained in a sample in the sample container.

Thus, compared to a method of measuring the sample solution kept stationary without stirring, the method according to the present invention allows the microorganisms to emit light in a very short time, enabling the amount of the microorganisms in ballast water to be easily and quickly measured. Furthermore, the thickness portion of the fluorescent emission is made thinner to significantly clarify the difference in the amount of light between the background and the fluorescent emissions from the microorganisms. As a result, the detection accuracy for the fluorescent emissions from the microorganisms is improved.

Additionally, an embodiment of the invention is characterized by including a filtering step between the light receiving step and the microorganism number estimating step, the filtering step filtering out noise of a low frequency component and noise of a high frequency component contained in the electric signal resulting from the conversion in the light receiving step.

Thus, before the electric signal is loaded into the control means, the filtering means filters out disturbance, allowing the electric signal commensurate with the amount of fluorescent emissions from the microorganisms to be definitely distinguished from the disturbance. This prevents a possible error in the measurement of the amount of microorganisms and a disadvantageous variation in measured values, enabling stable measurement.

Advantageous Effects of the Invention

The present invention can provide a method for examining microorganisms in ballast water and an examination apparatus for microorganisms which allow the amount of the microorganisms to be easily and quickly measured with high accuracy.

DESCRIPTION OF EMBODIMENTS

First Embodiment

Figure 1:
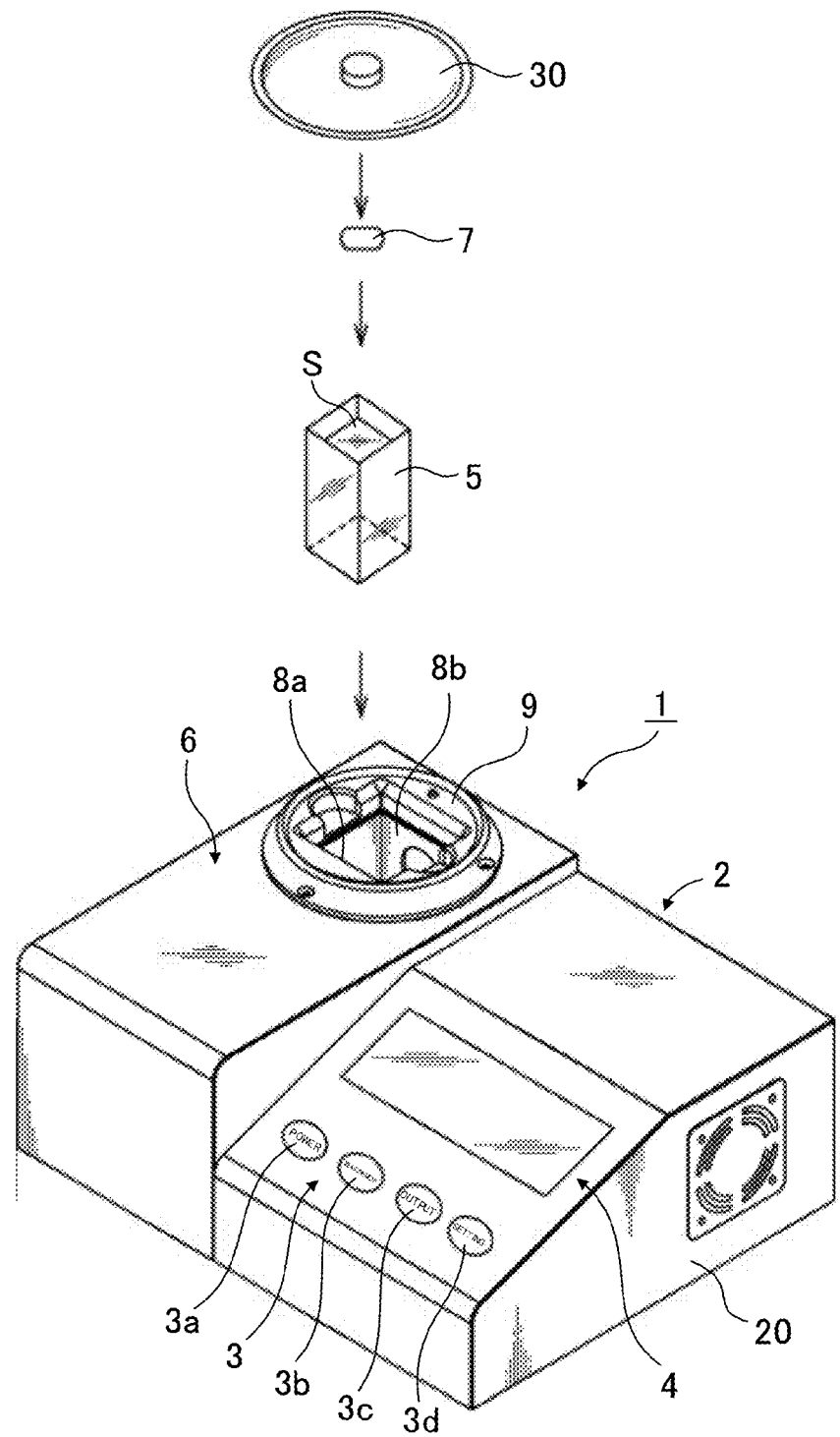
FIG. 1 is a perspective view generally depicting an examination apparatus for microorganisms according to embodiments of the present invention.
Figure 2:
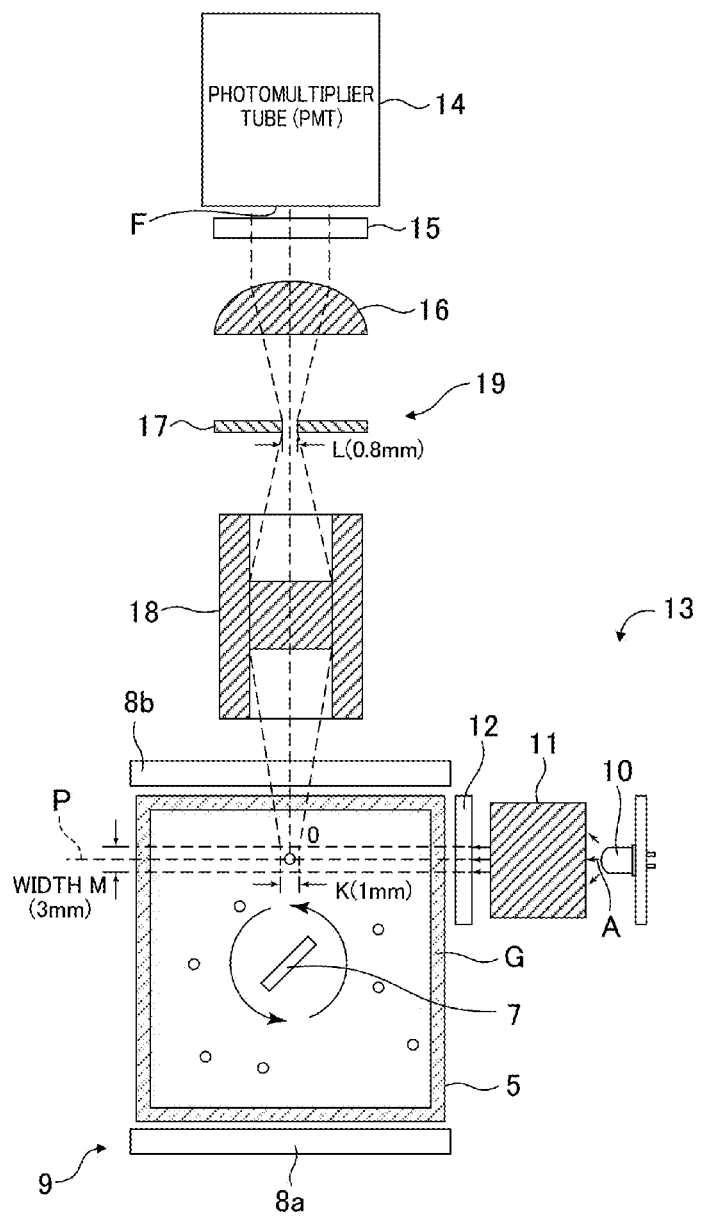
FIG. 2 is a schematic plane cross-sectional view of a measurement section according to the embodiments of the present invention.
Figure 3:
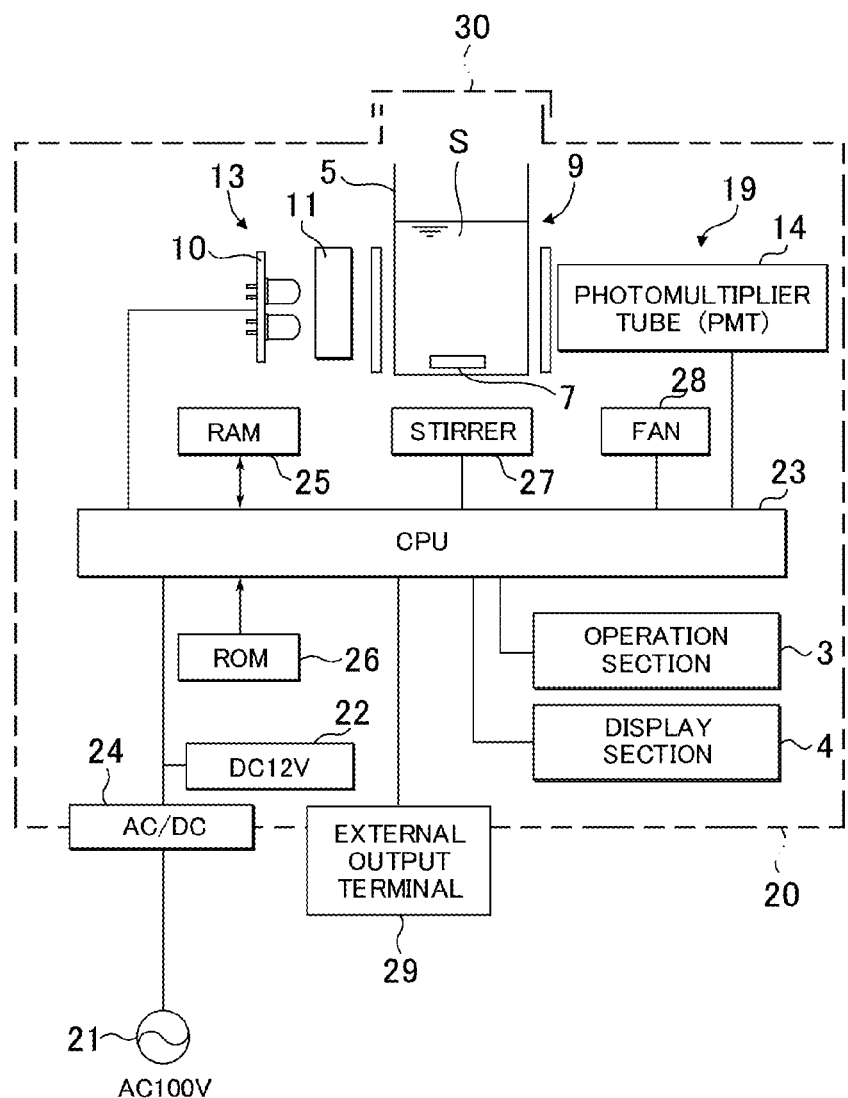
FIG. 3 is a block diagram depicting a general configuration of an examination apparatus for microorganisms according to a first embodiment of the present invention.

Embodiments of the present invention will be described with reference to the drawings. FIG. 1 is a perspective view generally depicting an examination apparatus for microorganisms according to the present embodiment. FIG. 2 is a schematic plane cross-sectional view of a measurement section according to the present embodiment. FIG. 3 is a block diagram depicting a general configuration of the examination apparatus for microorganisms according to the present embodiment.

As depicted in FIG. 1 and FIG. 2, an examination apparatus 1 according to the present invention includes, as main components, a main body section 2 incorporating a control mechanism such as a CPU board to perform an information processing operation and a statistical processing operation on measurement results and the like, an operation section 3 including an arrangement of operation buttons juxtaposed on the main body section 2, a display section 4 formed of a liquid crystal panel or the like in order to display the measurement results and the like, and a measurement section 6 that houses a batch sample container 5 formed of a transparent material that allows light to pass through (for example, glass, quartz, or an acrylic resin) to optically count the number of microorganisms in a sample solution S. Reference numeral 7 denotes a rotor that allows the sample solution S contained in the sample container 5. The rotor 7 is housed in the sample container 5 along with the sample solution S and an emission reagent, and is rotationally driven by a magnetic stirrer 27 incorporated in the measurement section 6 when the sample container 5 is housed in the measurement section 6. Thus, the number of microorganisms in the sample solution S can be counted while the sample solution S containing the sample and emission reagent in the sample container 5 is being stirred and mixed at a predetermined temperature. Compared to an examination apparatus for microorganisms which measures the sample solution kept stationary without stirring, the examination apparatus for microorganisms according to the present invention allows the microorganisms to emit light in a very short time, enabling the amount of the microorganisms in ballast water to be easily and quickly measured.

The examination apparatus 1 depicted in FIG. 1 is formed to have a width of 300 mm, a depth of 300 mm, a height of 100 mm, and a weight of approximately 2 to 4 kg. The examination apparatus 1 can be carried in a handheld trunk (not depicted in the drawings) to enable measurement in a ship or outdoors.

The batch sample container 5 formed of the material that allows light to pass through is shaped like a prism having a 50 mm×50 mm bottom surface and a height of 60 mm. The internal capacity of the sample container 5 at a water level of 40 mm is set to 100 ml (milliliters). The sample container 5 is not limited to such a prismatic shape but may be shaped like a cylinder or a cubic provided that an internal capacity of approximately 100 ml (milliliters) can be secured.

As depicted in FIG. 1, FIG. 2, and FIG. 3, the measurement section 6 includes a sample container housing section 9 that houses and holds the sample container 5, a light source section 13 that irradiates the sample container 5 with excitation light, and a light receiving section 19 that allows microorganisms stained with an emission reagent and floating in the sample container 5 to be observed using the excitation light radiated by the light source section 13. The light receiving section 19 electrically communicates with a CPU board 23 which counts the number of microorganisms in the sample solution S and which performs an information processing operation and a statistical processing operation on measurement results and the like.

The sample container housing section 9 includes holding plates 8a, 8b surrounding at least two surfaces of the sample container 5, and houses and holds the sample container 5 so as not to block radiation of light from the light source section 13.

As depicted in FIG. 2, the light source section 13 is disposed such that excitation light enters an irradiation target surface G of the sample container 5 along a normal AP. The light source section 13 includes a LED light source 10 disposed near the sample container housing section 9, parallel-light converting means 11 disposed in front of the LED light source 10 to convert diffusion light into parallel light (the parallel-light converting means 11 converts light from a LED into parallel rays of light impinging uniformly on a surface at the same angle), and an excitation light band pass filter 12 that irradiates the sample container 5 with excitation light including slit-like parallel rays of light.

Figure 8A:
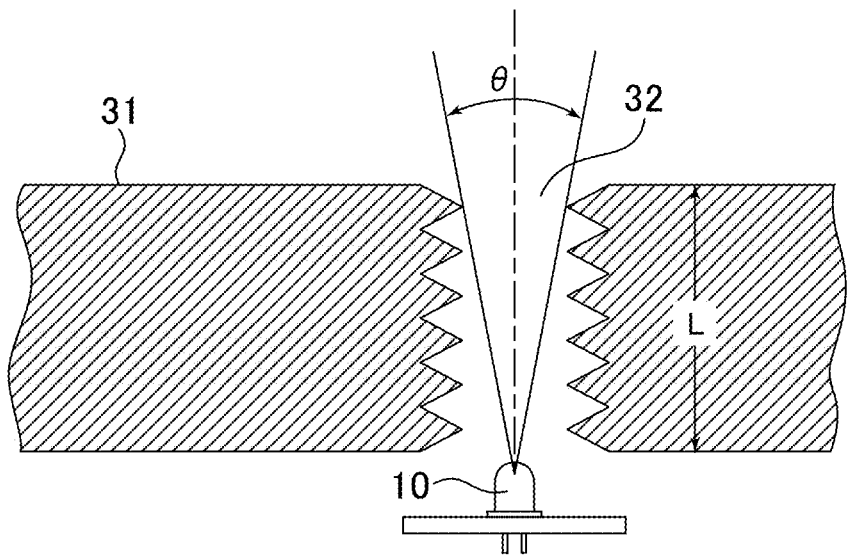
FIG. 8A is a schematic cross-sectional view depicting an embodiment of parallel-light converting means.

FIG. 8 is a schematic cross-sectional view depicting an embodiment of the parallel-light converting means 11. In an example depicted in FIG. 8A, the parallel-light converting means 11 is formed by drilling a threaded hole 32 with a predetermined diameter in a flat plate 31 with a predetermined thickness. The thickness L of the flat plate 31 and the hole diameter of the threaded hole are appropriately set in accordance with an optical path length. Thus, scattering light with an incident angle θ radiated by the LED light source 10 is converted into parallel light upon passing through the threaded hole 32. In the example depicted in FIG. 8A, optimum conditions for θ and L have been determined through tests on an SN ratio. For example, for M3 (the outer diameter of the threaded hole)×0.5 (pitch), θ is optimum at 9.5° and L is optimum at 15 mm.

Figure 8B:
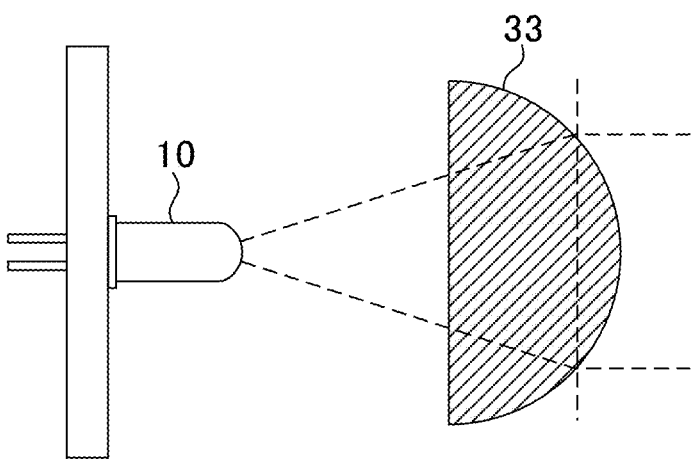
FIG. 8B is a schematic cross-sectional view depicting an embodiment of the parallel-light converting means.

The parallel-light converting means 11 depicted in FIG. 8B includes a convex lens 33 provided in front of the LED light source 10. Scattering light radiated by the LED light source 10 is converted into parallel light upon passing through the convex lens 33 to the exterior.

The light source section 13 according to the present embodiment uses the LED light source 10 as a light source. However, the present embodiment is not limited to the LED light source 10 but a parallel-light LED light source, a laser light source, or a light bulb which enables parallel light to be radiated may be used provided that the light source allows fluorescent substances contained in the microorganisms to be excited. Of course, when a parallel-light LED light source or a laser light source is used which enables parallel light to be radiated, the above-described parallel-light converting means 11 is unwanted.

As depicted in FIG. 2, the light receiving section 19 is provided so as to dispose a light receiving surface F at an angle orthogonal to excitation light traveling from the light source section 13 along the normal AP. Furthermore, the light receiving section 19 includes a photomultiplier tube (PMT) 14 arranged to receive fluorescence along an optical axis orthogonal to parallel light corresponding to excitation light radiated toward the sample container 5 by the LED light source 10, a fluorescence band pass filter 15 disposed in front of the photomultiplier tube (PMT) 14, a condensing lens 16 disposed in front of the fluorescence band pass filter 15, a slit 17 disposed in front of the condensing lens 16, and a relay lens 18 installed at the gap between the slit 17 and the sample container 5 to excite fluorescent substances contained in the microorganisms to condense and form the resultant fluorescence into an image.

Figure 9A:
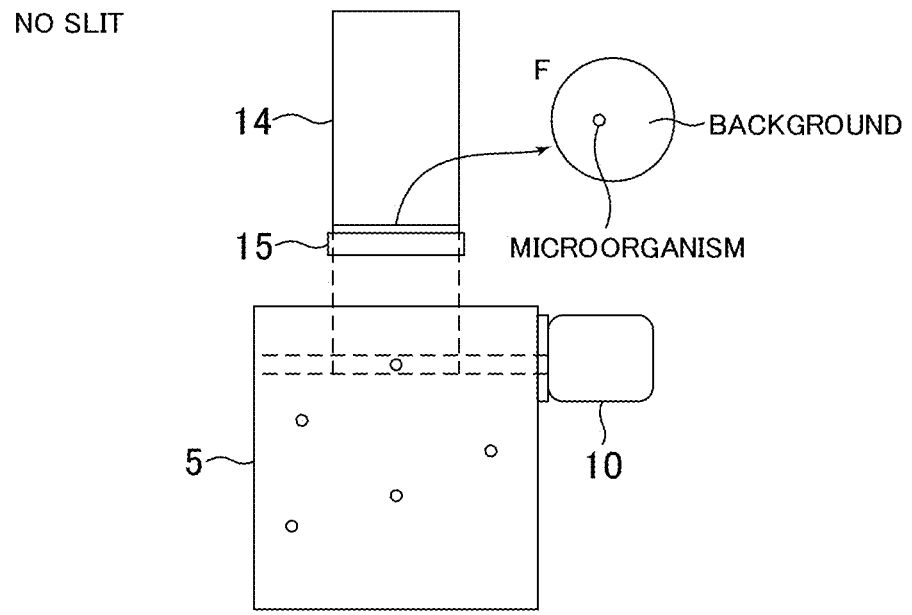
FIG. 9A is a diagram depicting the effect of the presence of slits which serves to narrow a viewing surface.
Figure 9B:
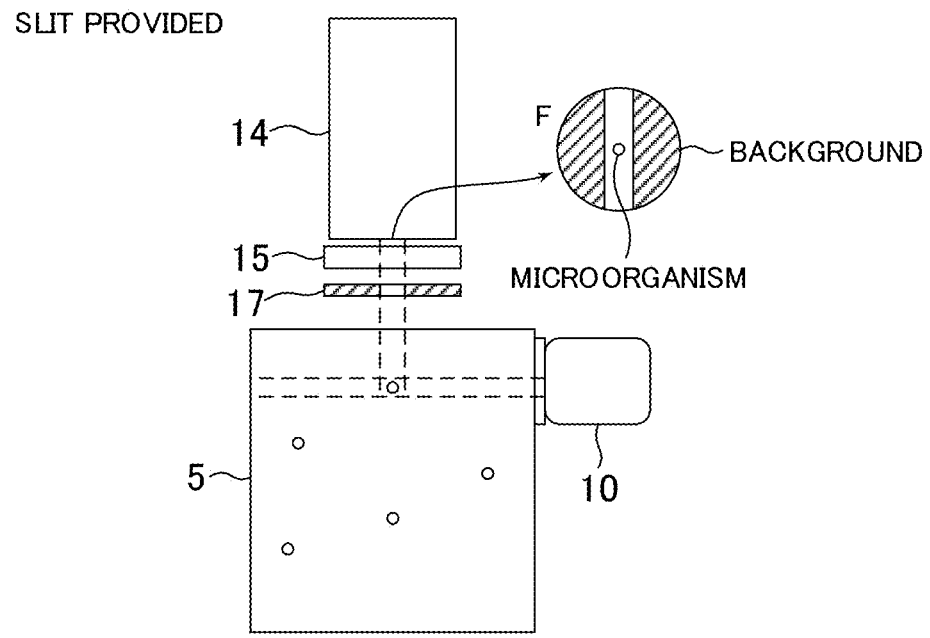
FIG. 9B is a diagram depicting the effect of the presence of slits which serves to narrow a viewing surface.

The slit 17 between the photomultiplier tube (PMT) 14 and the sample container 5 serves to narrow a viewing surface like a slit. That is, with no slit provided as depicted in FIG. 9A, a background is monitored for which a light receiving surface F is shaped like a circle. On the other hand, with a slit provided as depicted in FIG. 9B, a background is monitored for which the light receiving surface F is shaped like a vertically long slit corresponding to the circle except for a shaded portion. Thus, the light receiving area of the light receiving surface F decreases as in FIG. 9B, reducing the area of a fluorescent emission from the background. This increases the signal ratio of the fluorescent emissions from the microorganisms to the fluorescent emission from the background, improving the detection accuracy for the fluorescent emissions from the microorganisms.

In the illustrated example, the light receiving section 19 uses the photomultiplier tube (PMT) 14 as a light receiving sensor. However, the present embodiment is not limited to the photomultiplier tube (PMT) 14 but may adopt various photodetectors such as a silicon photodiode (SiPD) and an avalanche photodiode (APD) which allow detection of emissions from fluorescent substances contained in the microorganisms similarly to the photomultiplier tube (PMT).

Moreover, an electric control configuration for the examination apparatus 1 according to the present embodiment will be described with reference to FIG. 3. A CPU board 23 is disposed in the internal center of a housing 20 forming the main body section 2 to receive a supply of power from an AC power source 21 or a secondary battery 22 to analyze an electric output signal into which light has been converted by the photomultiplier tube (PMT) 14, determine whether or not the output signal has a brightness within any range, perform pulse counting on signals with any brightness, and perform on/off control on the LED light source 10. An AC/DC converter 24 is interposed between the AC power source 21 and the CPU board 23.

The CPU board 23 electrically connects to the photomultiplier tube (PMT) 14, the LED light source 10, a RAM 25 serving as a read and write storage section, and a ROM 26 serving as a read-only storage section. The CPU board 23 also electrically connects to a power button 3a, a measurement start button 3b, an external output button 3c, and a setting button 3d. The power button 3a is depressed to perform switch on/off control. The measurement start button 3b is depressed to start measurement. The external output button 3c is depressed to transfer data to an external printer or personal computer. The setting button 3d is depressed to switch the type of measurement (switch between measurement of L size microorganisms and measurement of S size microorganisms), change a determination criterion setting, change a threshold setting, or change a measurement time setting.

Besides, the CPU board 23 connects to a magnetic stirrer 27 that magnetically rotates the rotor 7, the display section 4 formed of a liquid crystal panel, a cooling fan 28 for control equipment such as the CPU board 23, and an external output terminal 29 such as an RS-232C.

Figure 4:
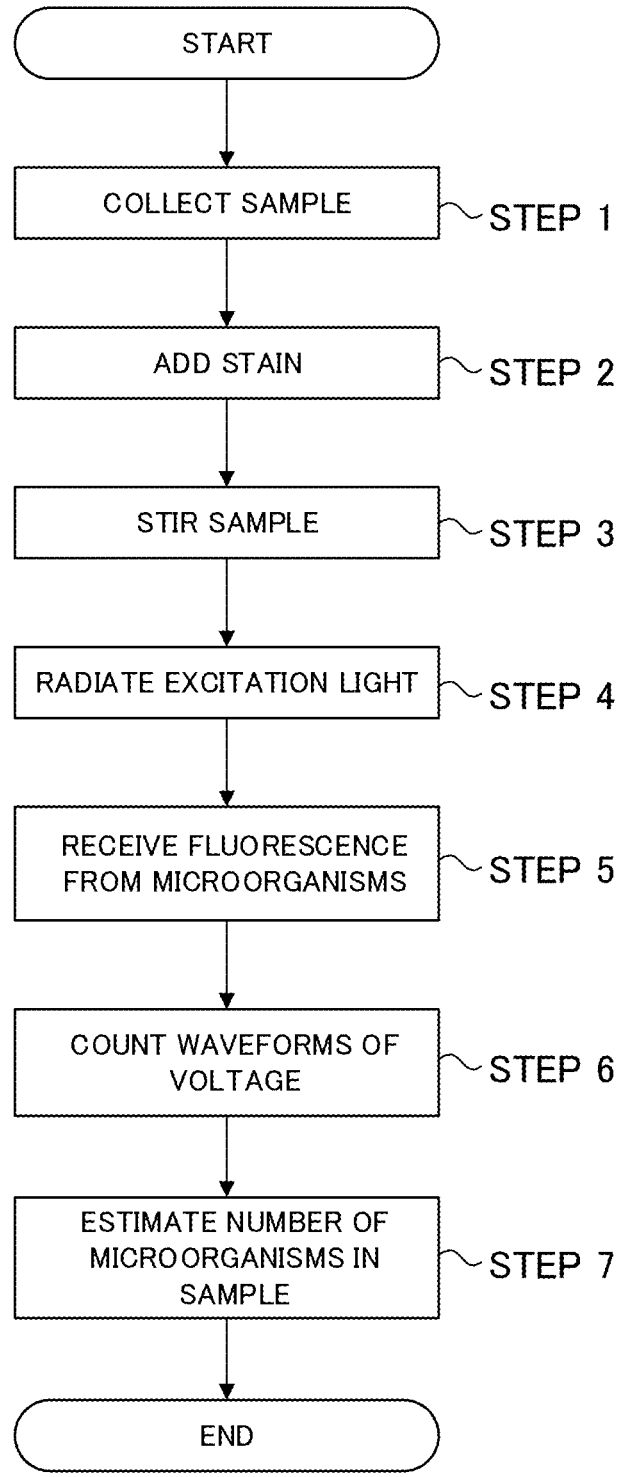
FIG. 4 is a flowchart depicting a measurement flow for the examination apparatus for microorganisms according to the first embodiment of the present invention.

FIG. 4 is a flowchart depicting a measurement flow. The effects of the above-described configuration will be described with reference to FIGS. 1 to 4.

First, an operator uses a pipette or the like to collect 100 ml of ballast water with a temperature of approximately 20° C. as a sample and introduces the sample into the sample container 5 (step 1 in FIG. 4). Then, the operator adds a fluorescent staining reagent into the sample container 5 (step 2 in FIG. 4). As the fluorescent staining reagent, Calcein-AM (manufactured by Promocell GMBH in Germany) or FDA, which is commonly known, may be used. The Calcein-AM tends to stain phytoplanktons, whereas the FDA tends to stain zooplanktons. Thus, when staining with a staining reagent is performed using a reagent that is a mixture of the Calcein-AM and the FDA, the staining time for the reagent can be reduced, enabling the time needed for the staining to be reduced to half of the conventionally needed time. Then, the operator introduces the rotor 7 into the sample container 5, houses the sample container 5 in the measurement section 6 of the examination apparatus 1, and places a cover 30 on the measurement section 6. Thus, preparation for measurement is completed. Then, when the power button 3a is depressed, the magnetic stirrer 27 incorporated in the measurement section 6 is driven to rotate the rotor 7, allowing the sample solution S to be stirred (step 3 in FIG. 4).

Then, the operator depresses the measurement start button 3b on the operation section. A predetermined time later, the LED light source 10 is turned on to irradiate the sample container 5 with light transmitted through the excitation light band pass filter 12. At this time, the sample container 5 is irradiated with light with a wavelength characterized to be 450 nm to 490 nm, and a specimen (microorganisms) in the sample container 5 emits fluorescence (step 4 in FIG. 4). The fluorescence passes through the fluorescence band pass filter 15 and is detected by the photomultiplier tube (PMT) 14 (step 5 in FIG. 4).

The photomultiplier tube (PMT) 14 utilizes a photoelectric effect to convert light energy into electric energy. The photomultiplier tube (PMT) 14 additionally has a current amplifying function and can sensitively detect fluorescent emission. The detected electric signal is transmitted to the CPU board 23, which then counts the number of received light waveforms with a value equal to or larger than a given threshold (step 6 in FIG. 4).

Moreover, the CPU board 23 estimates the number of microorganisms present in the 100-ml (milliliters) water in the sample container 5 based on the received light waveform count value to indicate, on the display section 4, whether or not the number of microorganisms meets the discharge standard (step 7 in FIG. 4).

Second Embodiment

A second embodiment is different from the first embodiment in that, in the second embodiment, filtering means 34 is provided between the light receiving section 19 and the CPU board 23. The remaining parts of the configuration are similar to the corresponding parts of the configuration of the first embodiment, and will thus not be described. The second embodiment will be described below based on the drawings.

Figure 5:
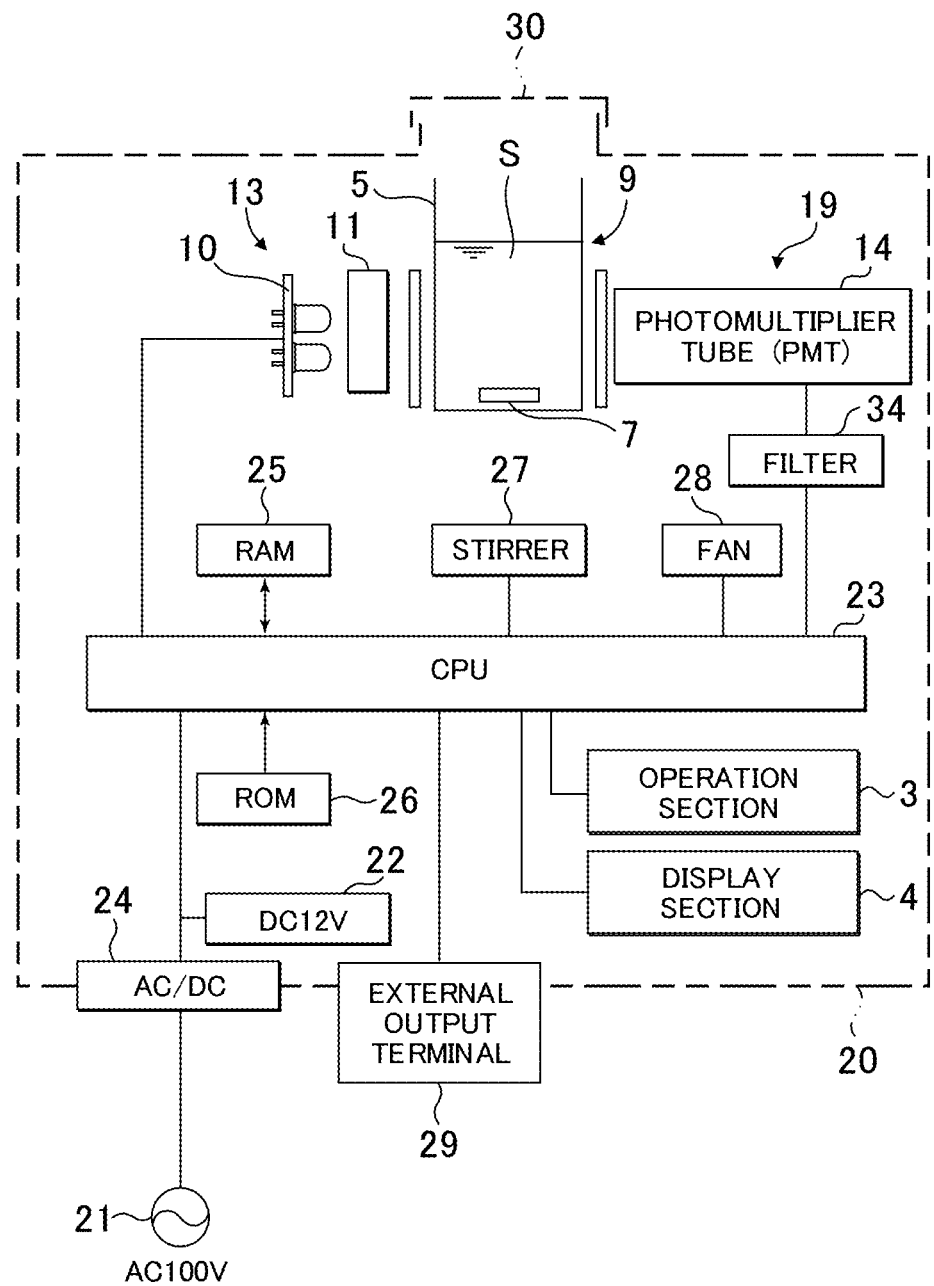
FIG. 5 is a block diagram depicting a general configuration of an examination apparatus for microorganisms according to a second embodiment of the present invention.

As depicted in FIG. 1, FIG. 2, and FIG. 5, the measurement section 6 includes the sample container housing section 9 that houses and holds the sample container 5, the light source section 13 that irradiates the sample container 5 with excitation light, and the light receiving section 19 that allows microorganisms floating in the sample container 5 and emitting light to be observed using the excitation light radiated by the light source section 13. The light receiving section 19 electrically communicates with the CPU board 23 via the filtering means 34. The CPU board 23 can count the number of microorganisms in the sample solution S based on electric signals from the light receiving section 19 and perform an information processing operation and a statistical processing operation on measurement results and the like.

Figure 6:
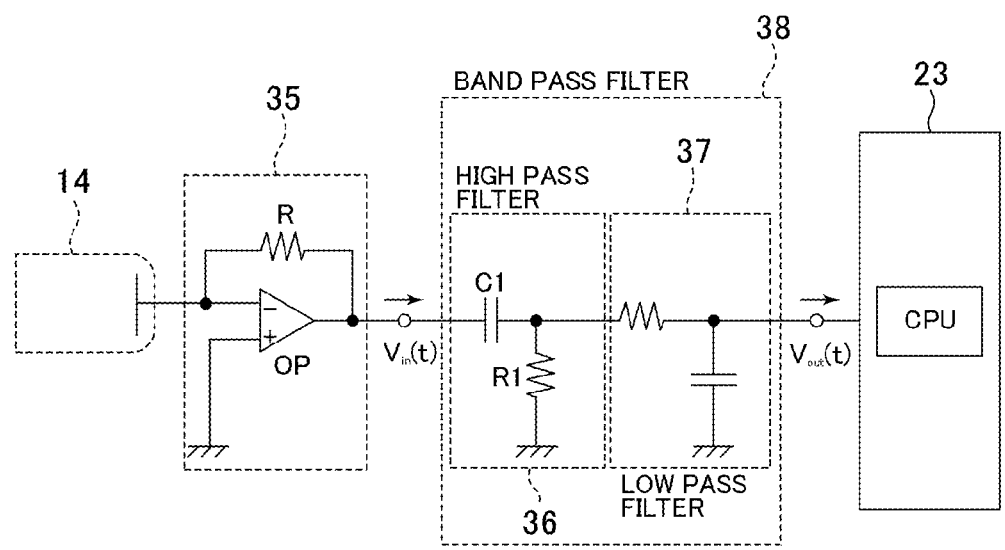
FIG. 6 is a diagram depicting an example of a circuit for filtering means according to the second embodiment of the present invention.

FIG. 6 is a diagram depicting an example of a circuit for the filtering means that is an important part of the present invention. As depicted in FIG. 6, an arithmetic amplifier 35, a high pass filter circuit 36, and a low pass filter circuit 37 are electrically connected together between the photomultiplier tube (PMT) 14 and the CPU board 23. The arithmetic amplifier 35 converts an output current generated in accordance with the amount of light received by the photomultiplier tube (PMT) 14, into a voltage, to enable even a minute current to be detected. Furthermore, the high pass filter circuit 36 is filtering means for avoiding attenuating components of an input signal with frequencies higher than a predetermined frequency and gradually reducing components with frequencies lower than a predetermined frequency. On the other hand, the low pass filter circuit 37 is filtering means for avoiding attenuating components of the input signal with frequencies lower than a predetermined frequency and gradually reducing components with frequencies higher than a predetermined frequency. Coupling the high pass filter circuit 36 and the low pass filter circuit 37 together results in a band pass filter circuit 38 that passes only a needed range of frequencies.

The arithmetic amplifier 35 has an operational amplifier OP and a resistor R. The high pass filter circuit 36 has a resistor R1 and a capacitor C1 electrically connected together. The low pass filter circuit 37 has a resistor R2 and a capacitor C2 electrically connected together. Thus, the arithmetic amplifier 35 converts an output current from the photomultiplier tube (PMT) 14 into a voltage. Then, when a signal Vin(t) is input to the band pass filter circuit 38 at an input side thereof, the band pass filter circuit 38 outputs, at an output side thereof, a signal Vout(t) from which an electric signal acting as disturbance has been filtered out. The disturbance has been clearly distinguished from the electric signal commensurate with the amount of fluorescent emissions received from the microorganisms. Consequently, when the filtered signal Vout(t) is input to the CPU board 23, no error occurs in the measurement of the amount of microorganisms and no disadvantageous variation occurs in measured values. As a result, stable measurement is enabled.

Figure 7:
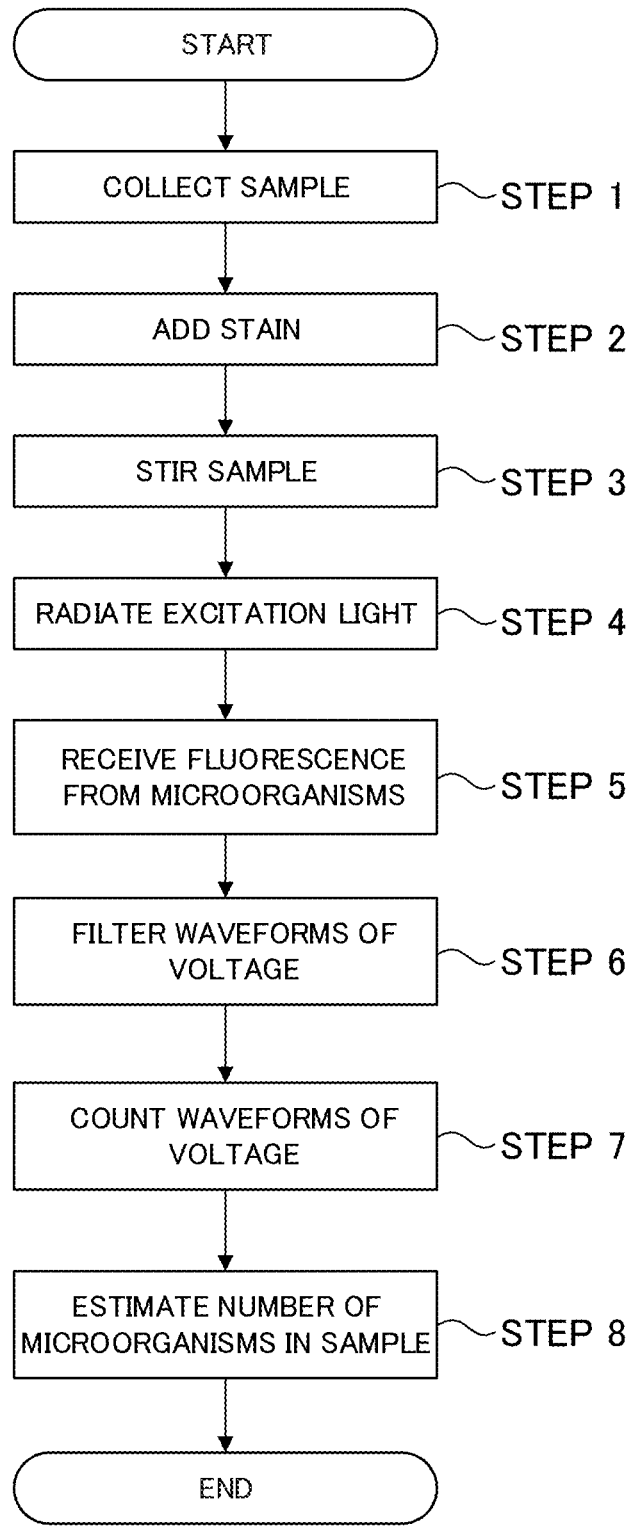
FIG. 7 is a flowchart depicting a measurement flow for the examination apparatus for microorganisms according to the second embodiment of the present invention.

FIG. 7 is a flowchart depicting a measurement flow. The effects of the above-described configuration will be described with reference to FIG. 1, FIG. 2, and FIGS. 5 to 7.

First, the operator uses a pipette or the like to collect 100 ml of ballast water with a temperature of approximately 20° C. as a sample and introduces the sample into the sample container 5 (step 1 in FIG. 7). Then, the operator adds a fluorescent staining reagent into the sample container 5 (step 2 in FIG. 7). As the fluorescent staining reagent, Calcein-AM (manufactured by Promocell GMBH in Germany) or FDA, which is commonly known, may be used. The Calcein-AM tends to stain phytoplanktons, whereas the FDA tends to stain zooplanktons. Thus, when staining with a staining reagent is performed using a reagent that is a mixture of the Calcein-AM and the FDA, the staining time for the reagent can be reduced, enabling the time needed for the staining to be reduced to half of the conventionally needed time. Then, the operator introduces the rotor 7 into the sample container 5, houses the sample container 5 in the measurement section 6 of the examination apparatus 1, and places the cover 30 on the measurement section 6. Thus, preparation for measurement is completed. Then, when the power button 3a is depressed, a magnetic stirrer 27 incorporated in the measurement section 6 is driven to rotate the rotor 7, allowing the sample solution S to be stirred (step 3 in FIG. 7).

Then, the operator depresses the measurement start button 3b on the operation section. A predetermined time later, the LED light source 10 is turned on to irradiate the sample container 5 with light transmitted through the excitation light band pass filter 12. At this time, the sample container 5 is irradiated with light with a wavelength characterized to be 450 nm to 490 nm, and a specimen (microorganisms) in the sample container 5 emits fluorescence (step 4 in FIG. 7). The fluorescence passes through the fluorescence band pass filter 15 and is detected by the photomultiplier tube (PMT) 14 (step 5 in FIG. 7).

The photomultiplier tube (PMT) 14 utilizes a photoelectric effect to convert light energy into electric energy. The photomultiplier tube (PMT) 14 additionally has a current amplifying function and can sensitively detect fluorescent emission. The detected electric signal is amplified by the arithmetic amplifier 35, and the amplified electric signal is input to the band pass filter circuit 36. Then, a signal is output from which an electric signal acting as disturbance has been filtered out (step 6 in FIG. 7). The signal from which the electric signal acting as disturbance has been filtered out is transmitted to the CPU board 23, which then counts the number of received light waveforms with a value equal to or larger than a given threshold (step 7 in FIG. 7).

Moreover, the CPU board 23 estimates the number of microorganisms present in the 100-ml (milliliters) water in the sample container 5 based on the received light waveform count value to indicate, on the display section 4, whether or not the number of microorganisms meets the discharge standard (step 8 in FIG. 7).

Examples of the present invention will be described below. First, verification tests on the examination accuracy of the examination apparatus for microorganisms according to the above-described embodiment will be described.

Example 1

Figure 10A:
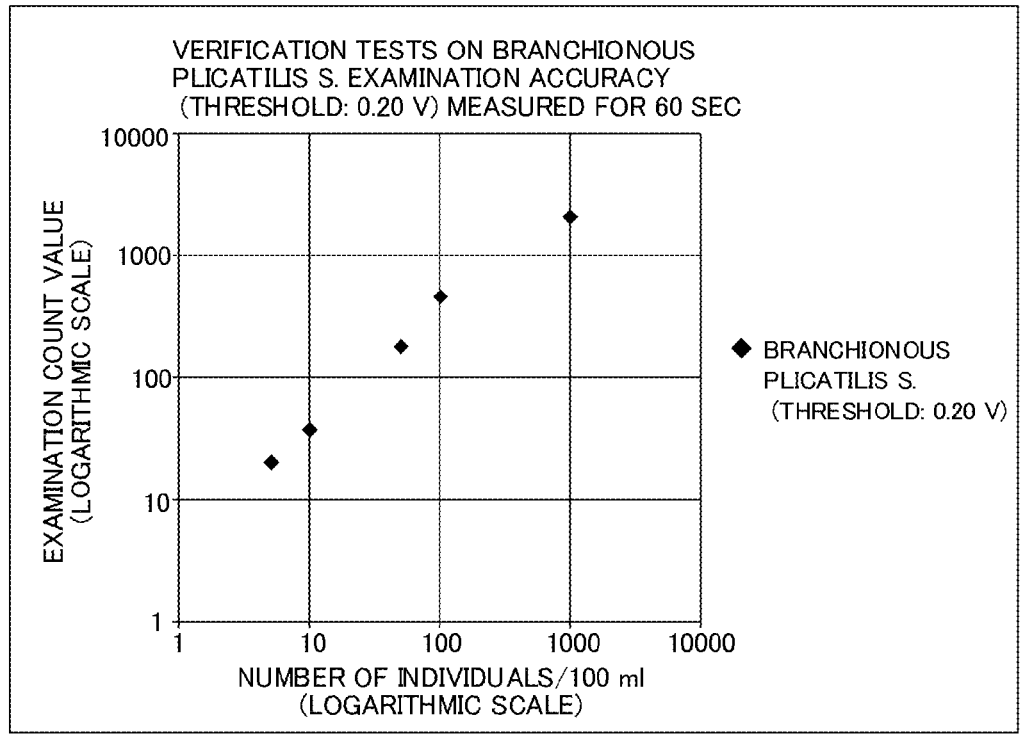
FIG. 10A is a graph depicting a correlation between the population of microorganisms and a light reception count in a photomultiplier tube (PMT).
Figure 10B:
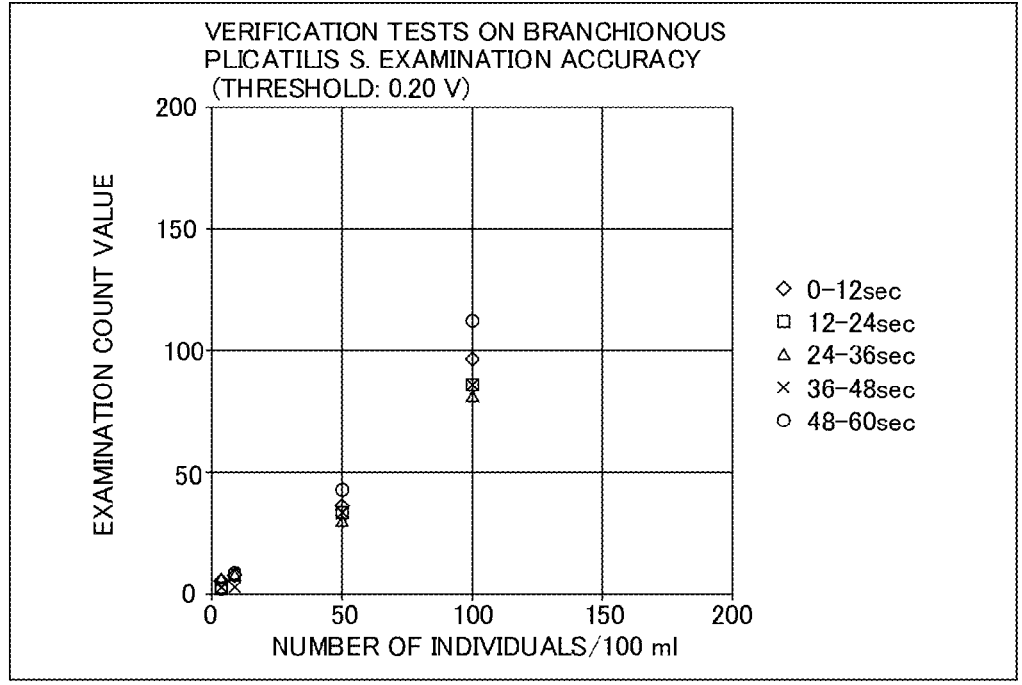
FIG. 10B is a graph depicting a correlation between the population of microorganisms and the light reception count in the photomultiplier tube (PMT).
Figure 11A:
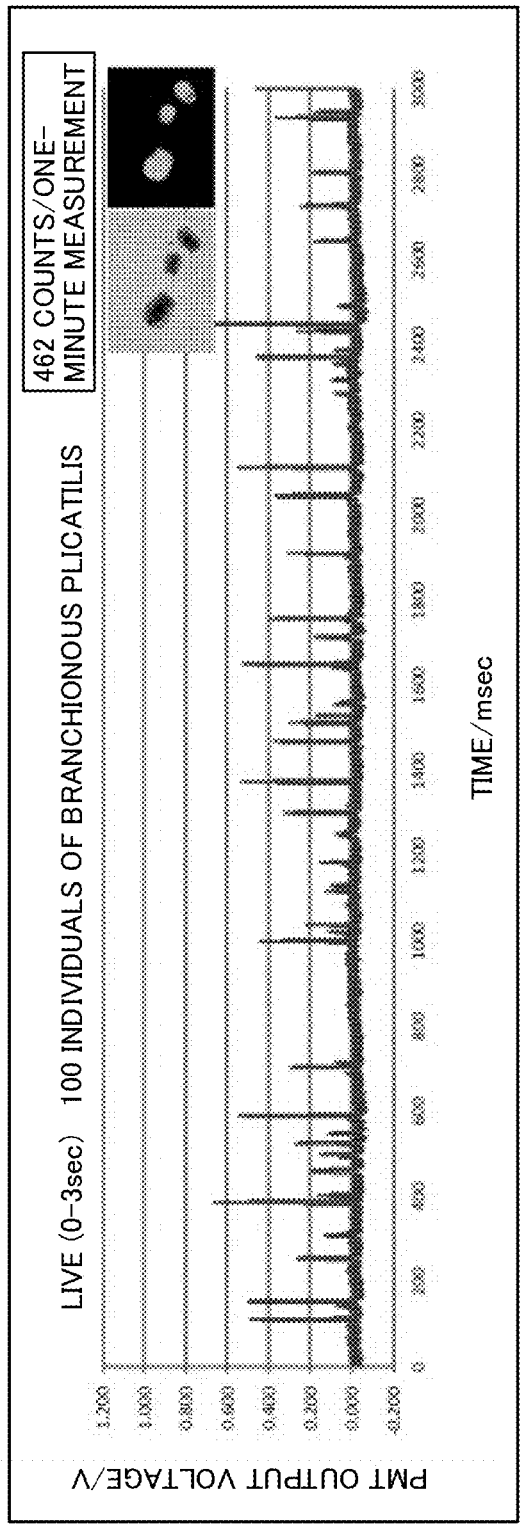
FIG. 11A is a graph indicating tests examining whether or not detection can be achieved based on whether microorganisms are alive or dead.
Figure 11B:
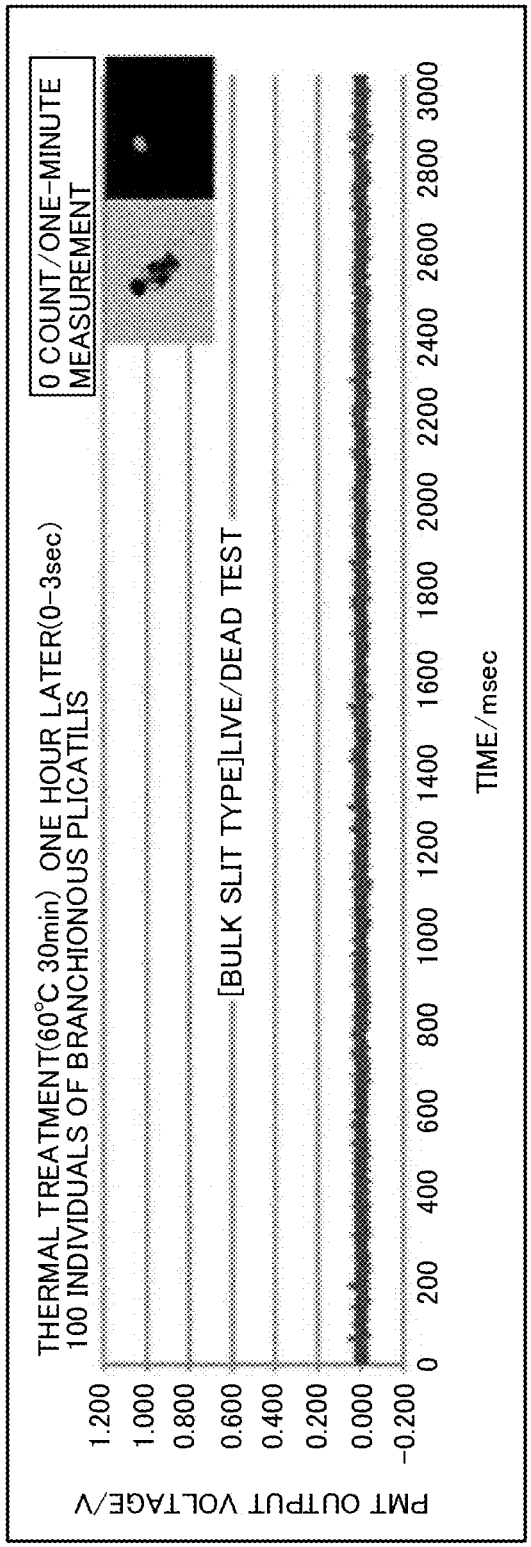
FIG. 11B is a graph indicating the tests examining whether or not detection can be achieved based on whether microorganisms are alive or dead.
Figure 11C:
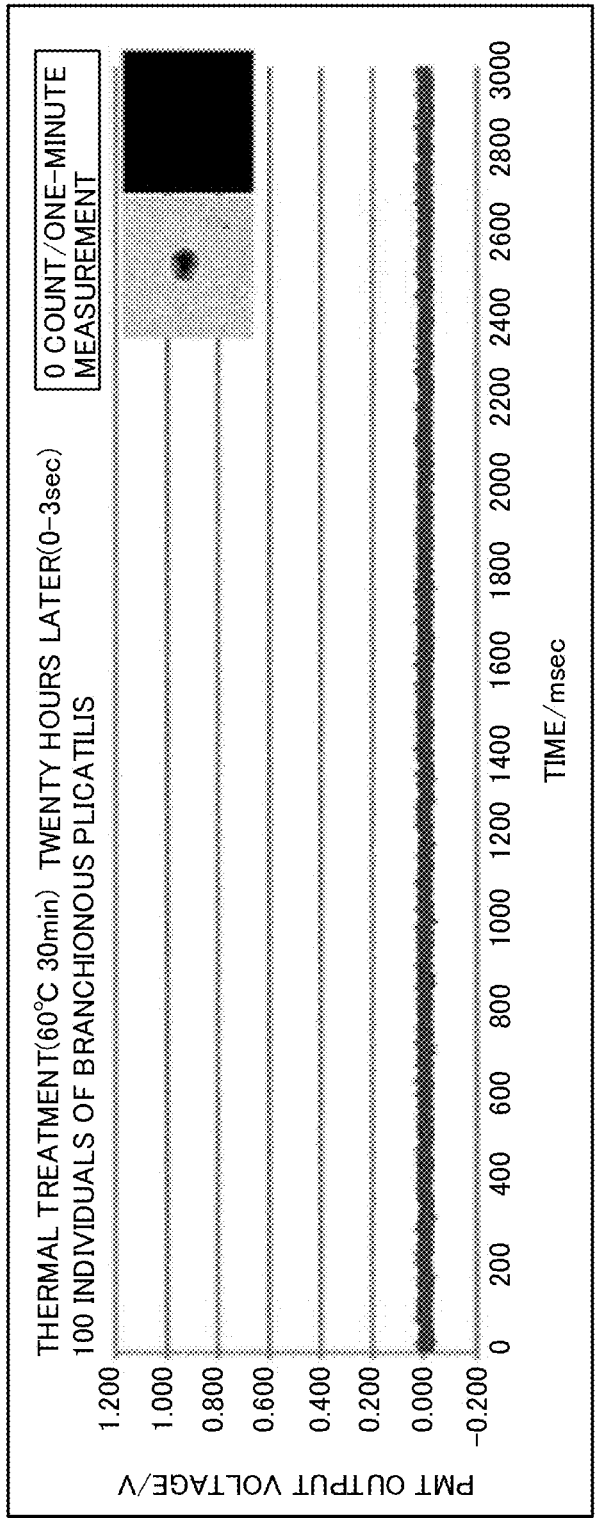
FIG. 11C is a graph indicating the tests examining whether or not detection can be achieved based on whether microorganisms are alive or dead.
Figure 11D:
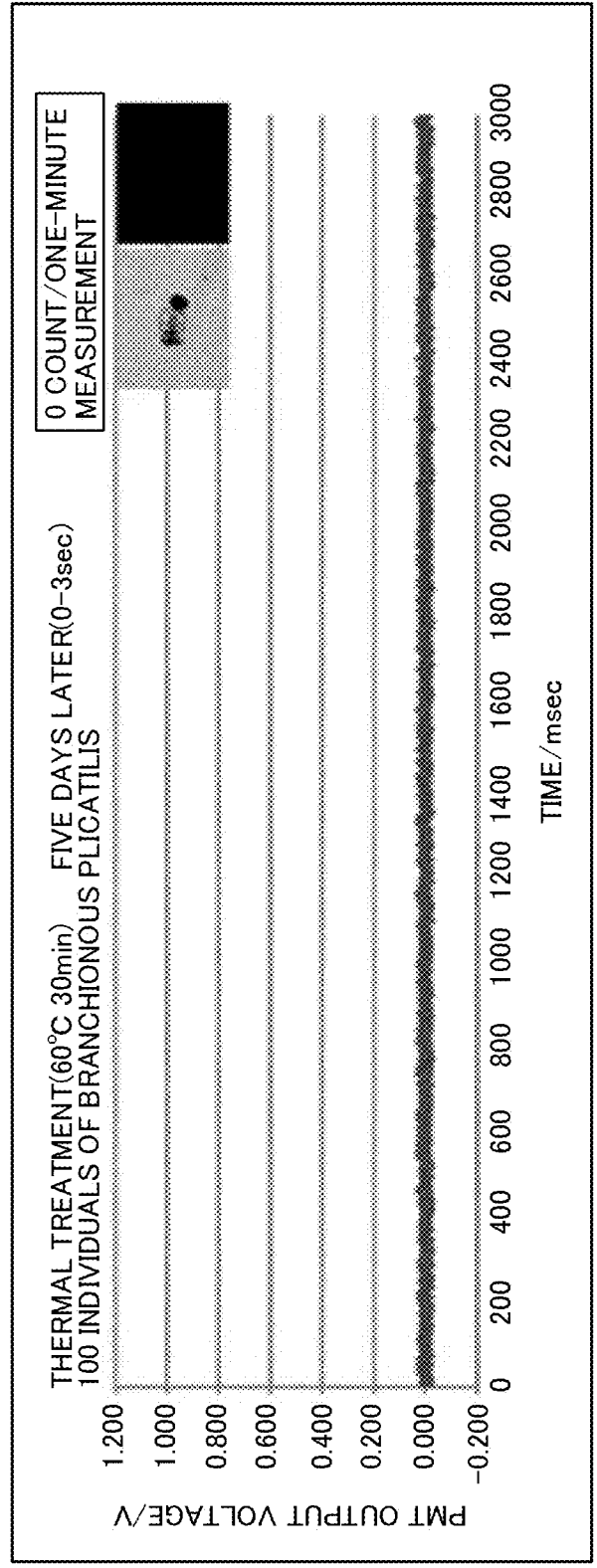
FIG. 11D is a graph indicating the tests examining whether or not detection can be achieved based on whether microorganisms are alive or dead.

The correlation between the population of microorganisms and the light reception count in the photomultiplier tube (PMT) was examined. Five, ten, fifty, one hundred, and one thousand individuals of *Brachionus plicatilis* s. (a minimum size of approximately 100 μm=L size organisms) were contained in a plurality of sample containers 5 (a capacity of 100 mL), respectively, and stained with the fluorescent staining reagent FDA (a concentration of 0.01 [millimole/litter]). As a result, the count of waveforms increased consistently with the number of individuals of the microorganisms contained, and a linear response was obtained for the five samples with five, ten, fifty, one hundred and one thousand individuals (see FIG. 10A, FIG. 10B). Thus, the population of the microorganisms present in the 100 mL of ballast water can be estimated from the count of waveforms obtained.

Example 2

Tests were conducted to determine whether or not detection was possible depending on whether microorganisms are alive or dead (see FIGS. 11A to 11D). *Brachionus plicatilis* s. (a minimum size of approximately 100 μm=L size organisms) subjected to a thermal sterilization treatment (heated at 60° C. for 30 minutes) was stained with the fluorescent staining reagent FDA (a concentration of 0.01 [millimole/litter]). Three samples were prepared one hour, twenty hours, and five days after the sterilization treatment and were each measured. As a result, no waveform with a value equal to or larger than a given threshold was found in the sterilized samples. This enables discrimination of samples not subjected to the sterilization treatment and containing microorganisms from samples subjected to the sterilization treatment and containing no microorganisms.

Example 3

The waveform of a voltage acquired before the filtering means is installed between the photomultiplier tube (PMT)

14 and the CPU board 23 is compared with the waveform of a voltage acquired after the installation.

Figure 12A:
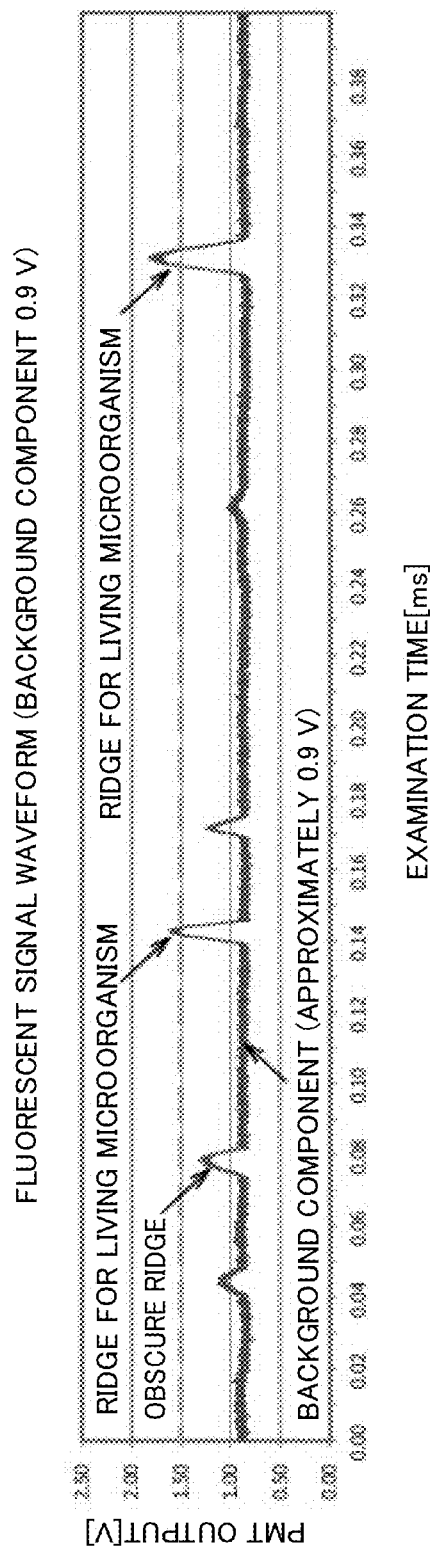
FIG. 12A is a graph depicting the waveform of a voltage acquired before installation of the filtering means.
Figure 12B:
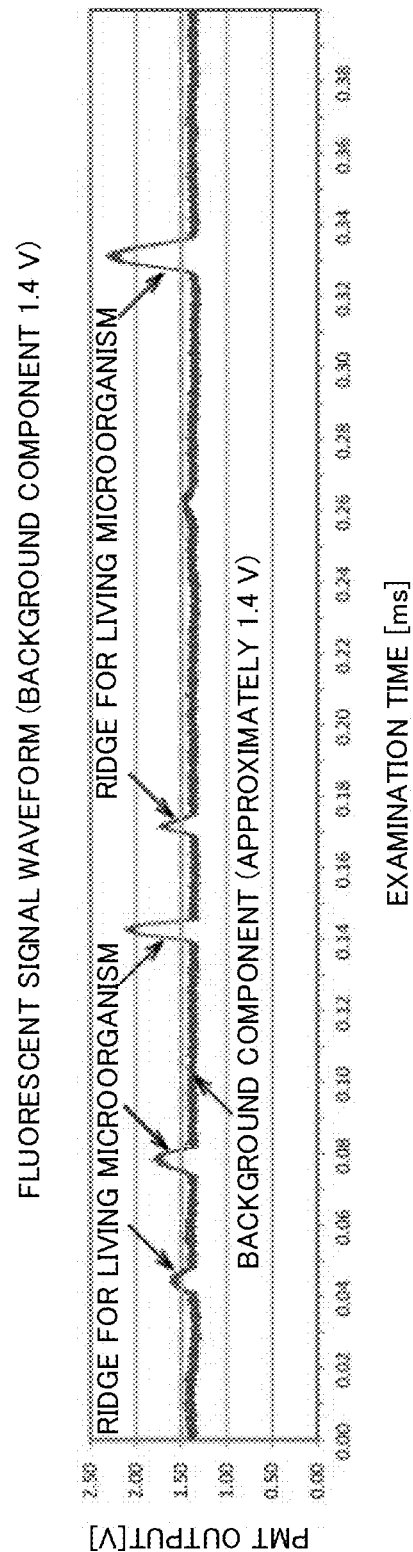
FIG. 12B is a graph depicting the waveform of the voltage acquired before installation of the filtering means.
Figure 12C:
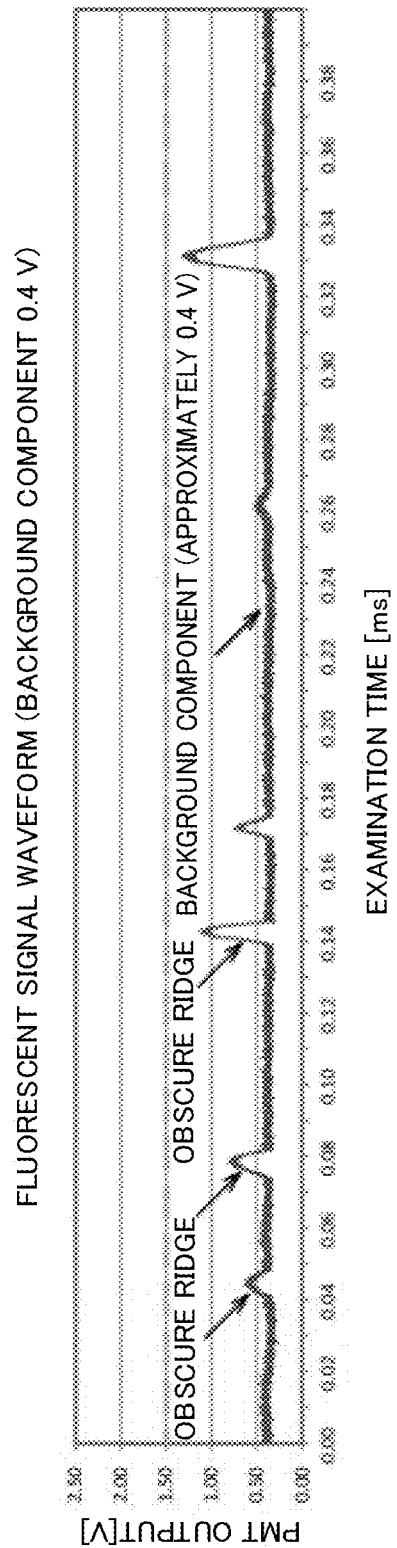
FIG. 12C is a graph depicting the waveform of the voltage acquired before installation of the filtering means.

FIG. 12 depicts the waveform of the voltage acquired before the filtering means is installed. The waveform of the acquired voltage depicted in FIG. 12A is a mixture of disturbance (approximately 0.9-V waveform of a background component), a definite ridge indicating a living microorganism exceeding the threshold, and an obscure ridge not exceeding the threshold. Furthermore, the waveform of the acquired voltage depicted in FIG. 12B is a mixture of disturbance (approximately 1.4-V waveform of a background component) and a definite ridge indicating a living microorganism exceeding the threshold. Moreover, the waveform of the acquired voltage depicted in FIG. 12C is a mixture of disturbance (an approximately 0.4-V waveform of a background component) and an obscure ridge not exceeding the threshold.

FIG. 13 depicts the waveform of the voltage acquired after the installation of the filtering means. The waveform of the acquired voltage depicted in FIG. 13A was acquired when only the high pass filter circuit 36 was installed, in order to eliminate the background component acting as disturbance. A comparison of this waveform with the waveform depicted in FIG. 12B indicates that the background component, which had been approximately 1.4 V, converged to 0 V and that the disturbance was eliminated.

Figure 13A:
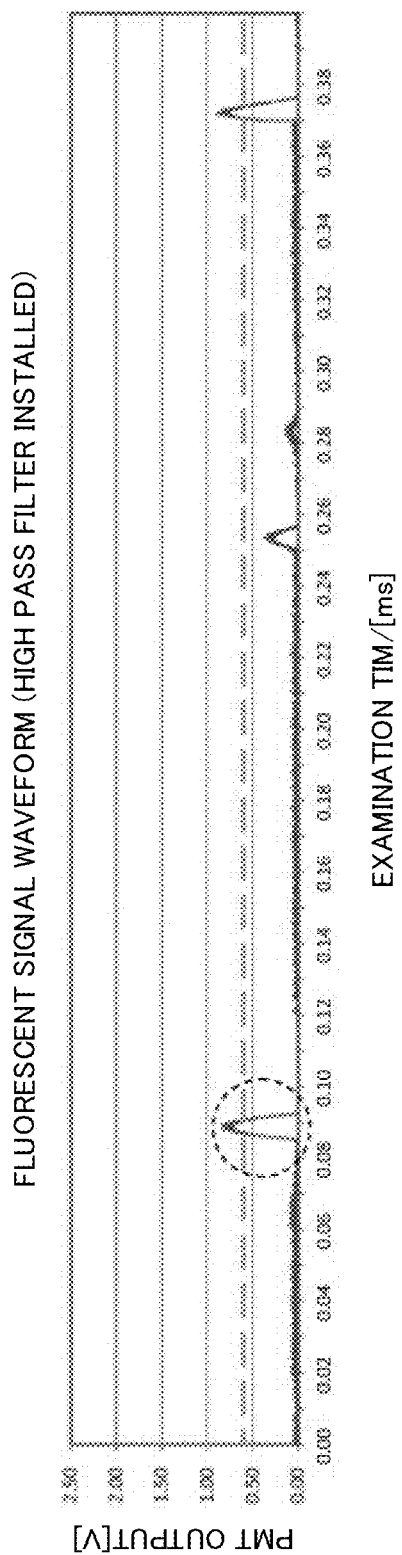
FIG. 13A is a graph depicting the waveform of a voltage acquired after installation of the filtering means.
Figure 13B:
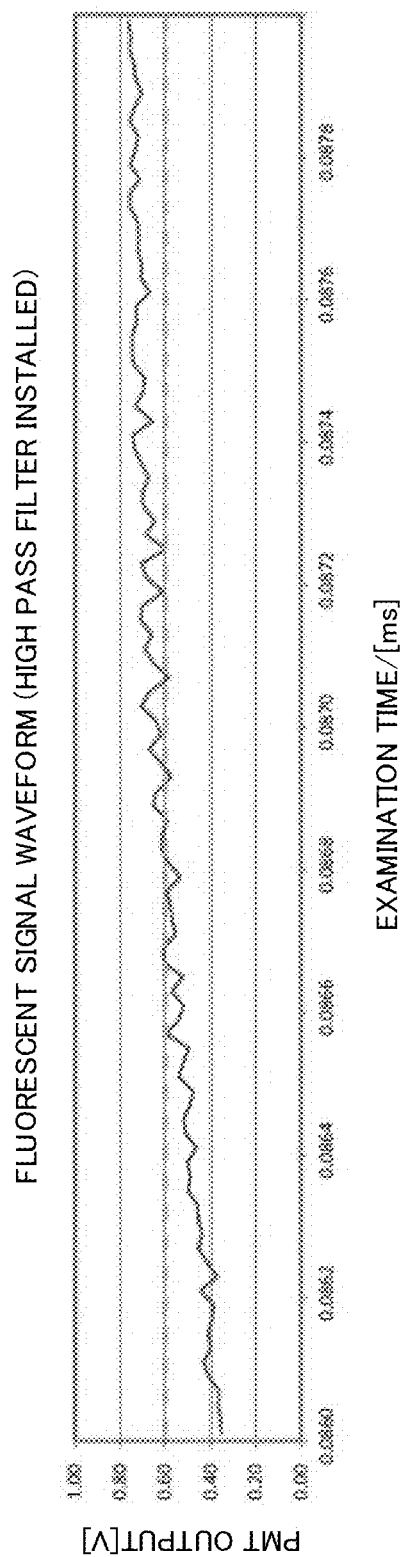
FIG. 13B is a graph depicting the waveform of the voltage acquired after installation of the filtering means.

The waveform in FIG. 13B is a rising waveform that is an enlarged waveform of a ridge encircled by a dashed line depicted in FIG. 13A. The waveform in FIG. 13B repeats moving up and down across the threshold, causing an increase in the magnitude of a measurement error. Thus, the low pass filter circuit 37 is desirably installed in order to eliminate such high-frequency waveforms.

Figure 13C:
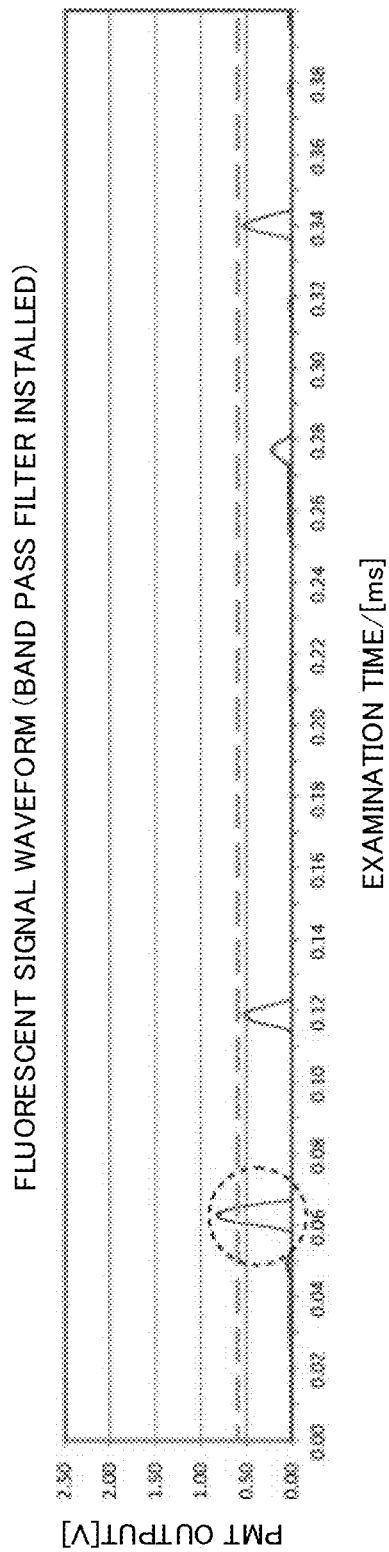
FIG. 13C is a graph depicting the waveform of the voltage acquired after installation of the filtering means.

The waveform of the acquired voltage depicted in FIG. 13C was acquired when the band pass filter circuit 38, including the high pass filter circuit 36 and the low pass filter circuit 37 coupled together, was installed, in order to eliminate disturbance and high-frequency waveforms. A comparison of this waveform with the waveform in FIG. 13A indicates that the high-frequency noise was eliminated to smooth the waveform.

Figure 13D:
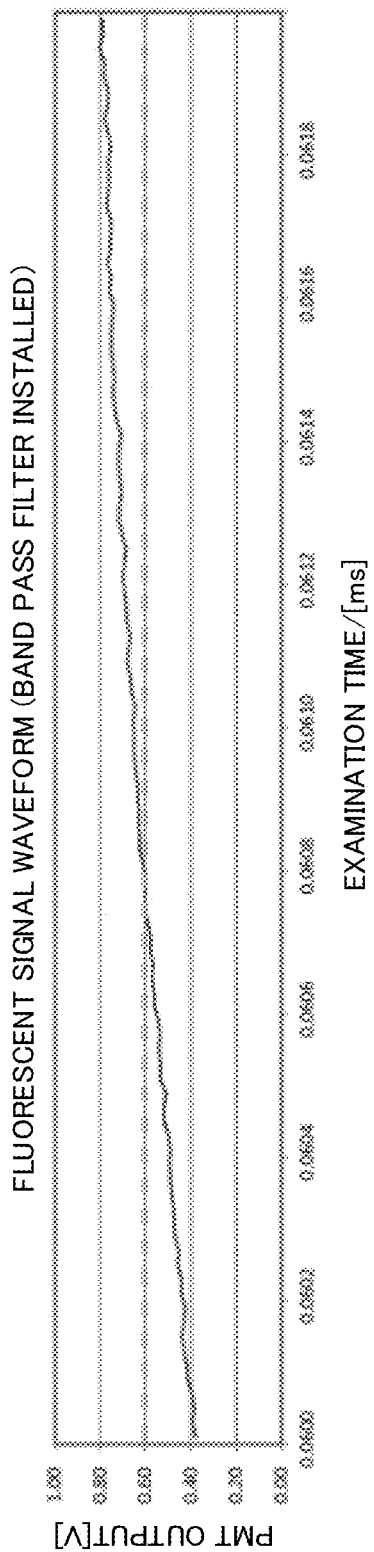
FIG. 13D is a graph depicting the waveform of the voltage acquired after installation of the filtering means.

The waveform in FIG. 13D is a rising waveform that is an enlarged waveform of a ridge encircled by a dashed line depicted in FIG. 13C. The waveform in FIG. 13D is smoothed and has no jagged waveform, and does not repeat moving up down across the threshold. This minimizes a measurement error to enable accurate measurement.

As described above, according to the present embodiments, the sample and the fluorescent staining reagent are added into the sample container 5, and then, the stirring and mixing means 7 stirs and mixes the sample solution. Thereafter, with the sample solution being stirred, excitation light is allowed to enter the irradiation target surface of the sample container, and moreover, the light receiving means receives fluorescent emissions from the microorganisms. Consequently, compared to an examination apparatus for microorganisms that measures the sample solution kept stationary without stirring, the examination apparatus for microorganisms according to the present embodiment allows the microorganisms to emit bright light in a very short time, enabling the amount of microorganisms in ballast water to be easily and quickly measured. Furthermore, the apparatus according to the present embodiment can be miniaturized, allowing manufacturing costs to be reduced.

Furthermore, before the electric signal is loaded into the control means, the filtering means filters out disturbance, allowing the electric signal commensurate with the amount of fluorescent emissions from the microorganisms to be definitely distinguished from the disturbance. This prevents a possible error in the measurement of the amount of the microorganisms and a disadvantageous variation in measured values, enabling stable measurement.

INDUSTRIAL APPLICABILITY

The present invention is applicable to an examination apparatus for microorganisms which checks whether or not the discharge standards are met when ballast water is discharged.

LIST OF REFERENCE NUMBERS

1 Examination apparatus
2 Main body section
3 Operation section
4 Display section
5 Sample container
6 Measurement section
7 Rotor
8 Holding plate
9 Sample container housing section
10 LED light source
11 Parallel-light converting means
12 Excitation light band pass filter
13 Light source section
14 Photomultiplier tube (PMT)
15 Fluorescence band pass filter
16 Condensing lens
17 Slit
18 Relay lens
19 Light receiving section
20 Housing
21 AC power source
22 Secondary battery
23 CPU board
24 AC/DC converter
25 RAM
26 ROM
27 Magnetic stirrer
28 Fan
29 External output terminal
30 Cover
31 Flat plate
32 Threaded hole
33 Cylindrical lens
34 Filtering means
35 Arithmetic amplifier
36 High pass filter circuit
37 Low pass filter circuit
38 Band pass filter circuit

What is claimed is:

1. A portable examination apparatus for microorganisms for estimating an allowable population of microorganisms contained and living in ballast water discharged from a ship from a number of microorganisms present in ballast water contained in a sample container and taken as a sample, and determining whether or not the number of microorganisms contained in the ballast water meets ballast water discharge standards, the apparatus comprising:

stirring and mixing means comprising a sample container formed of a material allowing light to pass through, for stirring and mixing the sample solution in the sample container;

an excitation light source that irradiates the sample container with excitation light, light receiving means for detecting light and converting the light into an electric signal;

light reception range setting means for setting a predetermined range of light to be received;

filtering means between the light receiving means and the control means;

counting means for converting the light received by the light receiving means into electrical signals and counting a number of luminescences occurring when microorganisms pass through the predetermined light reception range set by the light reception range setting means; and control means for calculating the amount of the microorganisms contained in a sample in the sample container and determining whether or not ballast water discharge standards are met from the number of luminescences counted by the counting means, wherein the sample solution is prepared by adding a fluorescent staining reagent that stains the microorganisms to the sample, the light receiving means detects a fluorescent emission from the sample solution resulting from irradiation with the excitation light from the excitation light source, and wherein the control means is capable of detecting a definite ridge in a waveform of the electrical signal from the light receiving means indicating presence of microorganisms in the sample in an amount exceeding a predetermined threshold and an obscure ridge indicating presence of microorganisms in an amount not exceeding the threshold in the sample, wherein the filtering means filters out noise of a low frequency component and a noise of a high frequency component contained in the electric signal from the light receiving means, wherein an operation section including a plurality of operating buttons is electrically connected to the control means, wherein the operating section includes a setting button that enables switching between different sizes of microorganisms to be measured, the stirring and mixing means, the excitation light source, the light receiving means, the filtering means, and the control means combined into a single integrated unit.

2. The examination apparatus for microorganisms according to claim 1, wherein the filtering means is a band pass filter with a high pass filter and a low pass filter coupled together.

3. The examination apparatus for microorganisms according to claim 1, wherein the excitation light source is disposed so as to irradiate the sample container with the excitation light in such a manner that the excitation light is orthogonal to the sample container, and the light receiving means is disposed so as to receive the fluorescent emission at an angle orthogonal to the excitation light from the excitation light source.

4. The examination apparatus for microorganisms according to claim 1, wherein a slit member is provided between the light receiving means and the sample container.

5. The examination apparatus for microorganisms according to claim 1, wherein parallel-light converting means for converting light from the excitation light source into parallel light is provided between the excitation light source and the sample container.

6. The examination apparatus for microorganisms according to claim 5, wherein the parallel-light converting means is formed by drilling a threaded hole in a flat plate.

7. The examination apparatus for microorganisms according to claim 5, wherein the parallel-light converting means is formed of a convex lens.

8. A method of estimating an allowable population of microorganisms contained and living in ballast water discharged from a ship from a number of microorganisms present in ballast water contained in a sample container and taken as a sample, and determining whether or not the number of microorganisms contained in the ballast water meets ballast water discharge standards using a portable examination apparatus that combines stirring and mixing means, an excitation light source, a light receiving means, filtering means, and control means in a single integrated unit, the method comprising:

a stirring and mixing step of stirring and mixing, in the sample container, the sample solution in which a fluorescent staining reagent that stains the microorganisms is added to a sample;

an excitation step of irradiating the sample container with excitation light;

a light receiving step of detecting a fluorescent emission from the sample container resulting from the irradiation with the excitation light and signal;

a light reception range setting step of setting a predetermined range of light to be received;

a filtering step of filtering out noise of a low frequency component and noise of a high frequency component contained in the electric signal resulting from the conversion in the light receiving step;

a counting step of converting the light received by the light receiving means into electrical signals and counting a number of luminescences occurring when microorganisms pass through the predetermined light reception range set in the light reception range setting step; and a microorganism number estimating step of calculating the amount of the microorganisms contained in a sample in the sample container from the number of luminescences counted in the counting step, wherein the control means is capable of detecting a definite ridge in a waveform of the electrical signal from the light receiving means indicating presence of microorganisms in the sample in an amount exceeding a predetermined threshold and an obscure ridge indicating presence of microorganisms in an amount not exceeding the threshold in the sample.

* * * * *